(12) United States Patent
Garner (10) Patent No.: US 7,183,394 B1
(45) Date of Patent: Feb. 27, 2007

(54) HELICAL NUCLEOPEPTIDES (76) Inventor: Philip P. Garner, 3376 Clarendon Rd., Cleveland Heights, OH (US) 44118

(*) Notice: Subject to any disclaimer, the term of this patent is extended or adjusted under 35 U.S.C. 154(b) by 668 days.

(21) Appl. No.: 10/110,017

(22) PCT Filed: Aug. 11, 2000

(86) PCT No.: PCT/US00/21845

§ 371 (c)(1),
(2), (4) Date: Mar. 28, 2002

(87) PCT Pub. No.: WO01/14398

PCT Pub. Date: Mar. 1, 2001

(51) Int. Cl.
C07H 21/02 (2006.01)
C07H 21/04 (2006.01)
C07H 21/00 (2006.01)
C12Q 1/68 (2006.01)

(52) U.S. Cl. .................. 536/23.1; 536/24.3; 536/25.3; 435/6

(58) Field of Classification Search ............... 536/23.1, 536/24.3, 25.3; 435/6
See application file for complete search history.

(56) References Cited

FOREIGN PATENT DOCUMENTS

WO    WO92/20702    * 11/1992

OTHER PUBLICATIONS

Garner et al. Modular Nucleic Acid Surrogates. Solid Phase Synthesis of Helical peptide NUcleic Acids ( PNAs) Organic Letters Aug. 12, 1999, vol. 1, No. 3 pp. 403-405.*
Scarfi et al. Biochemical and Biophysical Research Communications 236, 323-326 1997.*

* cited by examiner

Primary Examiner—Jezia Riley
(74) Attorney, Agent, or Firm—Fay Sharpe LLP (57) ABSTRACT The present invention relates to peptide-based nucleic acid surrogates (PNAs) having a repeating structure of $(AA^B\text{-}aa_n)_m$ and a particular secondary structure that can bind to particular single-stranded nucleic acid targets. Preferably the peptide-based nucleic acid surrogate has an alpha-helical secondary structure ($\alpha$PNA). Also, the present invention relates to the method of forming peptide-based nucleic acid surrogates having a particular secondary structure. The nucleic acid surrogates may be utilized for therapeutic (antisense, antigene), diagnostic (genetic), and molecular switching ($\alpha$PNA chips) applications.

21 Claims, 6 Drawing Sheets

HELICAL NUCLEOPEPTIDES

FIELD OF THE INVENTION

The present invention relates to the design, synthesis, and potential applications of α-helical peptide nucleic acids (αPNAs) which are new molecular constructs that merge the molecular recognition elements of nucleic acids with the predictable structural features of an α-helical peptide scaffold. These new peptide-based nucleic acid surrogates bind with high affinity and specificity to complementary single stranded DNA and are capable of binding to both single stranded RNA and double stranded DNA targets. The present invention is directed to the use of αPNAs for therapeutic (antisense, antigene), diagnostic (genetic), and molecular switching (αPNA chip) applications.

BACKGROUND OF THE INVENTION

In most DNA-regulatory proteins, α-helical subunits serve as the molecular scaffolding for presentation of key amino acid side chains to their specific nucleic acid binding sites. (Cf. Steitz, T. A. Q. Rev. Biophys. 1990, 23, 205). Sequence-specific binding of these α-helical binding domains to double-stranded DNA occurs in the major groove as a consequence of multiple interactions arrived at (combinatorially) through evolutionary selection. Despite work toward the elucidation of Nature's "code" for molecular recognition of double-stranded DNA, it is not yet feasible to rationally design a peptide structure that will bind to any particular DNA duplex. (Desjarlais, J. R., Ber, J. M. Proc. Natl. Acad. Sci. U.S.A. 1992, 89, 7345; Desjarlais, J. R., Berg, J. M. Proc. Natl. Acad. Sci. U.S.A. 1993, 90, 2256; Rebar, E. J., Pabo, C. O. Science 1994, 263, 671; Jamieson, A. C., Kim, S.-H., Wells, J. A. Biochemistry 1994, 33, 5689; Choo, Y., Klug, A. Proc. Natl. Acad. Sci. U.S.A. 1994, 91, 11163; Segal, D. J., Dreier, B., Beerli, R. R., Banbus, C. F. III; Proc. Natl. Acad. Sci. U.S.A. 1999, Vol. 96, 2758). On the other hand, molecular recognition of single-stranded nucleic acids via Watson-Crick (W-C) base pairing is quite predictable and provides the basis for antisense approaches to genetic manipulation. (Antisense Research and Application; Crooke, S. T.; Springer-Verlag: Berlin, 1998).

The pioneering discovery that the (2-deoxy)ribose phosphate framework of nucleic acids could be replaced by a much simpler polyamide backbone has spawned considerable interest in "peptide nucleic acids" (PNAs) and related constructs. (Dueholm, K. L., Nielsen, P. E. New J. Chem. 1997, 21, 19; Eriksson, M., Nielsen, P. E., Q. Rev. Biophys. 1996, 29, 369). However, the merger of an α-helical peptidyl scaffold with well-defined nucleobase molecular recognition patterns (W—C base pairing for single-stranded RNA and Hoogsteen base pairing for double-stranded DNA) has not been explored. A particular advantage of such hybrid structures, termed as an α-helical peptide-based nucleic acid or αPNA, give the opportunity to functionalize the peptide scaffold itself to enhance transport, hybridization, and other properties.

SUMMARY OF THE INVENTION

The present invention relates to the design, synthesis, and potential applications of α-helical peptide nucleic acids (αPNAs), which are new constructs that merge the molecular recognition elements of nucleic acids with the predictable structural features of an α-helical peptide scaffold. The described αPNAs bind with high affinity and specificity to complementary single-stranded DNA and are capable of binding to both single-stranded RNA and double-stranded DNA targets. Although there are examples of peptide based nucleic acid surrogates, the use of peptide secondary structure to achieve the nucleobase spacing required for base-pairing to helical nucleic acids is conceptually novel.

The αPNA platform has a major advantage over known art in that it allows for the ready incorporation of functionality to enhance binding (affinity, kinetics, specificity) and modify/introduce other properties (solubility, transport, stability). Also, multifunctional αPNAs may be designed for use as artificial nucleases, biosensors, and molecular switches.

BRIEF DESCRIPTION OF THE DRAWINGS

FIGS. 2 A–C show gel shift assay binding studies.

FIGS. 5 A–B are charts showing $T_m$ versus calculated octanol-$H_2O$ partition coefficients.

DETAILED DESCRIPTION OF THE PREFERRED EMBODIMENTS

The present invention relates to the design, synthesis, and potential applications of peptide-based nucleic acid surrogates having a secondary structure. Preferably, the secondary structure of the peptide-based nucleic acid surrogate is α-helical with the structure known as α-helical peptide nucleic acids (αPNAs) which are new molecular constructs that merge the molecular recognition elements of nucleic acids with the predictable structural features of an α-helical peptide scaffold.

Peptide nucleic acids (PNAs) having a particular secondary structure are generally defined by the following subunit of $(AA^B\text{-}aa_n)_m$, wherein AA is any natural or unnatural (including but not limited to configurational isomers) hydroxyl-containing amino acid including, but not limited to serine, threonine, homo-serine, etc.; aa is a natural or unnatural (including but not limited to configurational isomers) α-amino acid (including α-dialkylated α-amino acids); B is a natural nucleobase (i.e. B=adenine, cytosine, guanine, thymine, and uracil) or unnatural analog (ie. B=7-deazapurines, 5-alkynylpyrimidines, "G-clamp", glycosylated 5-hydroxymethylpyrimidines, etc.); n is the number of natural or unnatural α-amino acids, wherein $n \geq 1$; and m is the number of repeating units, wherein wherein $m \geq 1$.

PNAs can possess different secondary structure elements (e.g., α-helix, $3_{10}$ helix, $2.2_7$ ribbon, π helix, β ribbon, etc.) and are capable of sequence-specific binding to complementary single-stranded or double-stranded nucleic acid targets. A PNA can bind to complimentary double-stranded nucleic acid targets by strand invasion (i.e., partial denaturation of the double-stranded nucleic acid target) or by direct recognition of the duplex. Preferably, a PNA comprising an α-helical secondary structure (αPNA) is capable of sequence specific binding to single-stranded nucleic acid targets.

The preferred αPNA can also act as a functional αPNA, wherein the functional αPNA can be conjugated with various molecules and molecular systems, including but not limited to, fluorescent labeling tags, other peptides, particular molecules (e.g. biotin, etc.), DNA and RNA, etc.

Figure 1A:
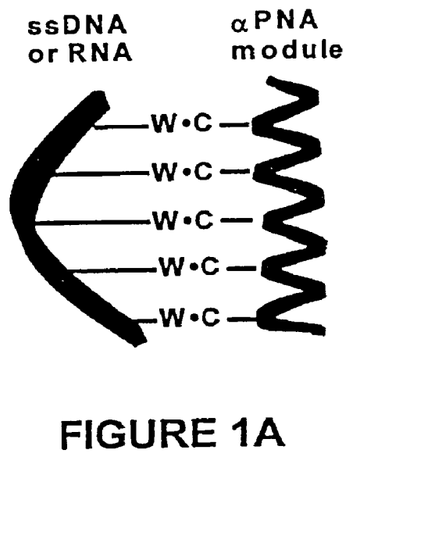
FIG. 1A is a Watson-Crick base pairing of the preferred αPNA module with a preferred single-stranded nucleic acid target.
Figure 1B:
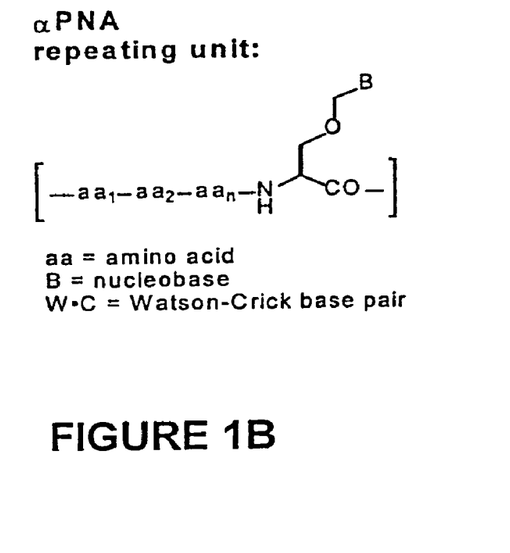
FIG. 1B is a preferred representation of an αPNA binding unit.

FIG. 1A shows a W-C (Watson-Crick) base pair binding between the preferred αPNA and complimentary single-stranded nucleic acid target, such as single-stranded DNA or RNA. FIG. 1B shows a preferred structural definition for an αPNA. In the preferred structural definition, the preferred hydroxyl-containing amino acid bound to a nucleobase B is serine, although any hydroxyl-containing amino acid is suitable.

Forming and identifying PNAs having a particular secondary structure, such as αPNA, include the following steps: (1) devising a practical synthesis of PNAs having particular secondary structures that incorporate the nucleoamino acid residue; and (2) purifying and characterizing of the resulting oligomeric PNAs having particular secondary structures; (3) evaluating of the ability of PNAs having particular secondary structures to bind to single-stranded nucleic acid; and (4) characterizing the structure of the resulting PNA•DNA complexes.

The synthesis of αPNA includes the following steps: (1) solid-phase peptide synthesis (SPPS) of an αPNA; and (2) cleaving the αPNA module from the resin with concomitant deprotection of all amino acid residues except cysteine to give a thiol-protected αPNA module. In addition, an optional third step of can be incorporated to link αPNA modules. Preferably, αPNA modules are linked by concomitant thiol deprotection and disulfide bond formation to produce a αPNA dimer, etc.

Protecting groups (PGs) are used to mask functional groups (FGs) that would interfere with, or not survive, a particular synthetic operation. A base-labile Fmoc PG is preferably chosen for the N-terminal amines. Acid-labile PGs, such as tert-butoxycarbonyl (Boc) and t-butyl ester, is preferably used for all sidechain functionalities except cysteine. For the cysteine residue, the $I_2$-labile acetamidomethyl (Acm) PG is preferably chosen to facilitate a separate disulfide formation step. (Veber, D. F.; Milkowski, J. D.; Varga, S. L.; Denkewalter, R. G.; Hirschmann, R. *J. Am. Chem. Soc.* 1972, 94, 5456–5461). Pyrimidine-containing serine derivatives are prepared by $I_2$-mediated nucleosidation of Fmoc-Ser(MTM)-OBn with silylated nucleobase. The acid-labile Rink amide linker (Rink amide linker=4-(2', 4'-dimethoxyphenylaminomethyl)phenoxyacetamido (Rink, H. *Tetrahedron Lett.* 1987, 28, 3787–3790)) is employed so that release of a fully extended peptide amide from the resin and removal of the acid-labile PGs could be achieved at the same time. Finally, DBU (DBU=1,8-diazabicyclo[5.4.0]undec-7-ene. Wade, J. D.; Bedford, J.; Sheppard, R. C. Tregear, G. W. *Pept. Res.* 1991, 4, 194) is used for Fmoc deprotectionCarpino's HATU (HATU=O-(7-azabenzotriazol-1-yl)-1, 1,3,3-tetramethyluronium hexafluoro-phosphate. Carpino, L. A. *J. Am. Chem. Soc.* 1993, 115, 4397–4398) reagent is used for all peptide couplings.

Either the manual or semi-automated SPPS of αPNAs can be utilized and provide αPNAs in 10–15% overall yield from commercially available Fmoc-Rink-MBHA resin after purification by gradient reverse-phase HPLC.

In order to form a disulfide linked αPNA dimer, $I_2$-mediated Acm deprotection/disulfide formation (Kamber, B.; Hartmann, A.; Eisler, K.; Riniker, B.; Rink, H.; Sieber, P.; Rittel, W. *Helv. Chim. Acta* 1980 63, 899–915) of the αPNA monomers is utilized and symmetrical tail-to-tail αPNA dimers are formed in good yield after HPLC purification.

Structure assignments for the αPNAs and αPNA dimers are confirmed by any known procedure such as MALDI-TOF or ESI mass spectrometry, and circular dichroism (CD) spectroscopy.

A further analyses of the production of αPNAs is disclosed in Garner, P., Dey, S., Huang, Y., and Zhang, X., *Org. Lett.* Vol. 1; No. 3, 1999, 403–405, herein incorporated by reference.

αPNA modules with as few as five nucleobases can bind with high affinity to complimentary single-stranded nucleic acid targets in a sequence-specific manner. The ability of an αPNA to bind to a single-stranded nucleic acid target can be evaluated via thermal denaturation and gel retardation experiments. For a detailed explanation of binding affinities of αPNA to complimentary nucleic acid targets, see Garner, P., Dey, S., and Huang, Y., *J. Am. Chem. Soc.* 2000, 122, 2405–2406, herein incorporated by reference.

An important aspect of αPNA•DNA complexation is the preferred directionality of binding, with the "parallel" (N/5') orientation favored both thermodynamically (deduced from $T_m$ data) and kinetically (deduced from amount of hysteresis) over the "antiparallel" (N/3') orientation. This is analogous to the well-known antiparallel (5'/3') strand orientation which is generally observed in nucleic acid duplexes. The parallel complex Ac-CTCCT•d($A_3$GAGGA$A_3$) possesses different a secondary structure from the antiparallel counterpart Ac-CTCCT•d($A_3$AGGAG$A_3$), which is evident from their CD profiles, particularly in the 230–290 nm region where the interaction of asymmetrically-disposed nucleobases is expected dominate the CD spectrum. (Johnson, W. C., Jr. in *Circular Dichroism and the Conformational Analysis of Biomolecules*, Fasman, G. D. Ed. Plenum Press: New York, 1996). The spectrum of the complex formed from an αPNA with a symmetrical base sequence (Ac-CCTCC), capable of forming either a parallel or antiparallel complex, is also consistent with the parallel orientation. αPNAs may be N-capped to obtain enhanced affinity and orientational specificity with complementary nucleic acid targets. For a detailed explanation of N-capped αPNAs, see Garner, P., Huang, Y, Dey, S. "Enhancement of αPNA Binding Affinity and Specificity via Hydrophobic Interactions" (unpublished).

Binding studies show that changing the peptide backbone can affect both the affinity and kinetics of αPNA binding to a nucleic acid target such as DNA. Combinatorial techniques are useful to explore the relationship between αPNA amino acid diversity and sequence-specific hybridization. The success of combinatorial techniques will depend largely on the development of an adequately sensitive and specific screen for hybridization. While there are numerous examples of binding assays for nucleic acid and peptide libraries, (Pirrung, M. C. *Chem. Rev.* 1997, 97, 473–488; Schultz, J. S. *Biotechnol. Prog.* 1996, 12, 729–743; Gold, L.; Polisky, b.; Uhlenbeck, o.; Yarus, M. *Annu. Rev. Biochem.* 1995, 64, 763–797; Pinilla, C.; Appel, J.; Blondelle, S.; Dooley, C.; Dörner, B.; Eichler, J.; Ostresh, J.; Houghten, R. A. *Biopolymers (Peptide Science)* 1995, 37, 221–240; Geysen, H. M.; Meloen, R. H.; Barteling, S. J. *Proc. Natl. Acad. Sci. USA* 1984, 81, 3998–4002) relatively little work has been done on screening hybridization of nucleic acid surrogates. (King, D. J.; Ventura, D. A.; Brasier, A. R.; Gorenstein, D. G. *Biochemistry* 1998, 37, 16489–16493).

"Immobilized nucleic acid hybridization" has become a common technique in molecular biology. This assay is based on Watson-Crick base-pairing and can be customized to screen αPNA libraries so that one can quickly identify compounds exhibiting high affinity towards immobilzed complementary nucleic acid targets. Since only the structure of the peptide backbone is to be varied, the nucleobase sequence of the αPNA will remain fixed. Thus, the effect of αPNA structure variation on hybridization using a single immobilized oligonucleotide target can be evaluated. The αPNAs can be "tagged" with a suitable fluorophore and, after hybridization, the high-affinity αPNAs bound to the nucleic acid would give an easily-detected fluorescent signal. An anologous FISH experiment has been reported with fluorophore-tagged Nielsen PNAs conjugated to a solubility-enhancing amino acid. (Gildea, B. D.; Casey, S.; Mac-Niell, J.; Perry-O'Keef, H.; Sørensen, D.; Coull, J. M. *Tetrahedron Lett.* 1998, 39, 7255–7258). Later, the "optimal" αPNA structure is selected from the initial pool of "hits" using a high-stringency assay like UV-melting.

A fluorescence based in situ hybridization assay for αPNAs has been developed. The results demonstrate that this analytical technique can be used to identify αPNAs that bind to DNA with high affinity and is suitable for screening αPNA libraries synthesized by combinatorial techniques.

Various flourophores may be utilized in the fluorescence-based in situ hybridization assay for αPNA libraries. Preferably, the BODIPY (Aleshkov, S. B.; Fa, M.; Karolin, J.; Strandberg, L.; Johansson, L. B.-Å.; Wilczynsha, M.; Ny, T. *J. Biol. Chem.* 1996, 271, 21231–21238) fluorophore is used since it has no residual charge that may influence the hybridization of the αPNA and nucleic acid. Either thiol- or amine-reactive BODIPY dyes can be used depending on which stage the fluorophore is to be incorporated into the αPNA.

For a further discussion regarding hybridization studies, see Huang, Y., Garner, P. "Flourescence-Based in situ Hybridization (FISH) Assay for Screening αPNA Libraries" (unpublished).

The synthesis of purine-containing αPNAs is relatively difficult because of the ease with which acid-catalyzed depurination occurs. It was found that a catalytic amount of ceric ammonium nitrate (CAN) (Hwu, J. R.; Jain, M. L.; Tsay, S.-C.; Hakimelahi, H. *Tetrahedron Lett.* 1996, 37, 2035–2038) can be used to remove the Boc group from the purine-containing modules under mild, neutral (oxidizing) conditions without depurination. These conditions will necessitate changing the cysteine protecting group (if one wishes to make disulfide-linked dimers) since the Acm group will also be susceptible to oxidative degradation. It is now possible to synthesize αPNAs that contain all 4 naturally-occuring nucleobases and study their hybridization properties.

The present invention is further illustrated by the following examples. It is to be understood that the present invention is not limited to the examples, and various changes and modifications may be made in the invention without departing from the spirit and scope thereof.

EXAMPLES

Demonstration that αPNA Binds to Complementary Single-Stranded DNA with High Affinity and in a Sequence Specific Manner The prototype αPNA design incorporated amino acid residues that were known to favor an α-helical formation:

backbone 1 (b1)=Ac-Cys$^{Acm}$-Gly-Ser$^B$-Asp-Ala-Glu-Ser$^B$-Ala$_2$-Lys-Ser$^B$-Ala$_2$-Glu-Ser$^B$-Ala-Aib-Ala-Ser$^B$-Lys-Gly-NH$_2$;

backbone 1' (b1')=Ac-Aib-Gly-Ser$^B$-Asp-Ala-Glu-Ser$^B$-Ala$_2$-Lys-Ser$^B$-Ala-Glu-Ser$^B$-Ala-Aib-Ala-Ser$^B$-Lys-Cys$^{Acm}$-NH$_2$).

The α-helical secondary structure (~26%) of these backbone 1 αPNAs in the absence of DNA was confirmed by circular dichroism (CD) studies in H$_2$O. Both the N-terminal linked (b1) and C-terminal-linked (b1') cysteine dimers formed complexes with d(A$_{10}$) in H$_2$O (Table 1, entries 1 and 2). The latter complex had a T$_m$ that was 12° C. higher than the former suggesting a thermodynamically preferred backbone orientation. The homothymine b1αPNAs required a relatively long incubation period (up to 4 days at 4° C. until constant absorbance was reached) due to the slow kinetics of annealing. Accordingly, no reassociation was observed during the cooling phase of the thermal denaturation experiments. By substituting cytosine (3H-bonds per C•G base pair) for thymine (2H-bonds per T•A base pair) in b1, even the monomeric C$_5$(b1) module was found to form a stable complex with d(TA$_3$G$_5$A$_3$T) (SEQ ID NO.: 1) in H$_2$O (entry 6). However, no binding was observed between these species in TE-buffer (10 mM Tris-HCl+1 mM EDTA, pH 7.0) even after 4 days of incubation. For comparison, d(T$_{10}$)•d(A$_{10}$) had a T$_m$ of 13° C. and d(C$_5$)•d(TA$_3$G$_5$A$_3$T) had a T$_m$ of 19° C. under optimal DNA•DNA binding conditions (pH 7 buffer, 150 mM NaCl). These results suggested that both C$_5$(b1) and the T$_5$(b1)-dimers, which are expected to have net charges of −1 and −2 respectively at neutral pH, may be experiencing some charge—charge repulsion with the polyanionic DNA targets thus slowing down the rate of hybridization.

In order to accelerate the rate of hybridization of αPNAs and single-stranded DNA, a new αPNA backbone was designed in which the negatively charged Asp and Glu residues were replaced with Lys:

backbone 2 (b2)=Ac-Cys$^{Acm}$-Lys-(Ser$^B$-Ala$_2$-Lys)$_4$-Ser$^B$-Gly-Lys-NH$_2$;

backbone 2' (b2')=Ac-Lys$_2$-(Ser$^B$-Ala$_2$-Lys)$_4$-Ser$^B$-Gly-Cys$^{Acm}$-NH$_2$).

This modification resulted in αPNAs having a net positive charge at neutral pH and was expected to enhance nonspecific binding to negatively charged DNA prior to sequence-specific base-pairing. (Cf. Corey, D. R. *J. Am. Chem. Soc.* 1995, 117, 9373–9374). Thus, both the T$_5$(b2)- and T$_5$(b2')-dimers formed complexes that exhibited well-defined melting curves in TE-buffer after only an overnight incubation period (entries 3 and 4) and, unlike b1 and b1', did not show a significant difference in stability. Even the T$_5$(b2) module hybridized with d(A$_{10}$) (SEQ ID NO.: 2)—albeit weakly as expected for a complex held together by only A•T base pairs (entry 5). Also, b2 αPNAs that contained cytosine resulted in remarkably stable αPNA•DNA complexes. For example, C$_5$(b2)•d(TA$_3$G$_5$A$_3$T) exhibited a T$_m$ of 54° C. in TE-buffer and no hysteresis was observed in the cooling curve. This implies that equilibration is being achieved during the cooling cycle. This T$_m$ is 20° C. higher than that of C$_5$(b1)•d(TA$_3$G$_5$A$_3$T) in H$_2$O (compare entries 6 and 7) and 35° C. higher than the corresponding DNA•DNA duplex (in TE-buffer+150 mM NaCl). Indeed, faster and stronger hybridization was observed for all matched cytosine-containing complexes formed with b2 αPNAs and complementary single-stranded DNAs with equilibrium dissociation constants (K$_d$) in the micromolar range. (Marky, L. A.;

Breslauer, K. J. *Biopolymers* 1987, 26, 1601–1620). Added salt was expected to disrupt favorable charge—charge interactions between cationic αPNAs and anionic DNA. Accordingly, while $C_5(b2) \cdot d(TA_3G_5A_3T)$ did exhibit a $T_m$ of 49° C. in TE-buffer+150 mM NaCl, no reassociation was observed during the cooling run. The presence of flanking bases on the DNA target strand also resulted in complexes with higher $T_m$ (compare entries 7 and 8), as well as greater hypochromicity and less hysteresis. Incorporation of mismatches into the αPNA (entries 7 and 10) resulted in a marked lowering of $T_m$ for the complexes, a result which is consistent with sequence-specific base recognition. Furthermore, the parallel orientation (N-terminus of αPNA adjacent to the 5'-end of DNA or N/5') resulted in a higher $T_m$ when compared to the antiparallel alternative (entries 11 and 12). The melted antiparallel (N/3') complex did not reassociate during the cooling cycle indicating slower binding kinetics relative to the parallel orientation.

TABLE 1

| Entry | αPNA | DNA sequence | $T_m$ (° C.) |
|---|---|---|---|
| 1. | $T_5(b1')$-dimer | $d(A_{10})^1$ | 39 |
| 2. | $T_5(b1')$-dimer | $d(A_{10})^1$ | 51 |
| 3. | $T_5(b2)$-dimer | $d(A_{10})^1$ | 46, 54[a] |
| 4. | $T_5(b1')$-dimer | $d(A_{10})^1$ | 46, 57 |
| 5. | $T_5(b2)$ | $d(A_{10})^1$ | 17 |
| 6. | $C_5(b1)$ | $d(TA_3G_5A_3T)^2$ | 34 |
| 7. | $C_5(b2)$ | $d(TA_3G_5A_3T)^2$ | 54 |
| 8. | $C_5(b1)$ | $d(G_5)$ | 35 |
| 9. | CCTCC(b2) | $d(A_3GGAGGA_3)^3$ | 49 |
| 10. | CCTCC(b2) | $d(TA_3G_5A_3T)^2$ | 38 |
| 11. | CCTCC(b2) | $d(A_3AGGAGA_3)^4$ | 32 |
| 12. | CCTCC(b2) | $d(A_3GAGGAA_3)^5$ | 37 |

[a]TWO-step melting was observed.
[1](SEQ. ID NO.: 2)
[2](SEQ. ID NO.: 1)
[3](SEQ. ID NO.: 3)
[4](SEQ. ID NO.: 4)
[5](SEQ. ID NO.: 5)

Figure 2A:
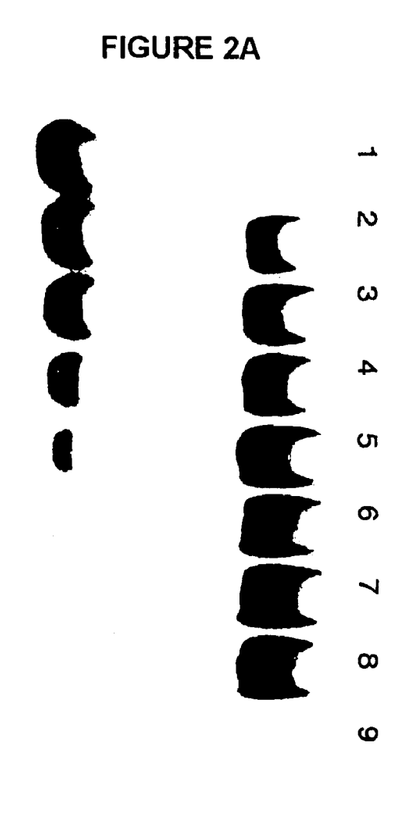
Figure 2B:
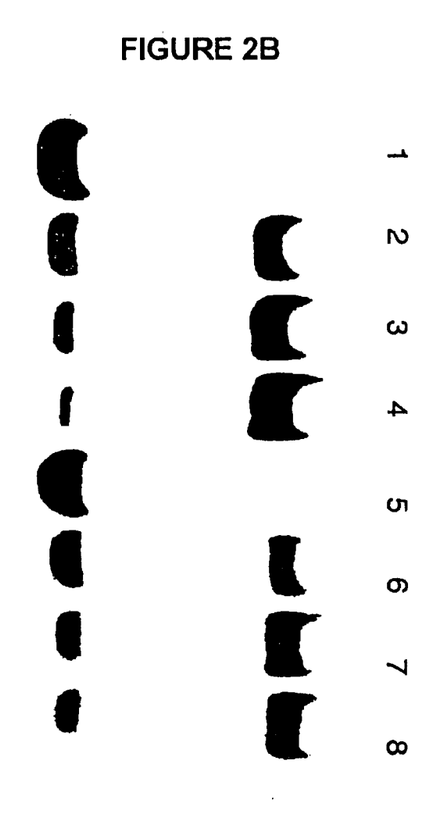
Figure 2C:
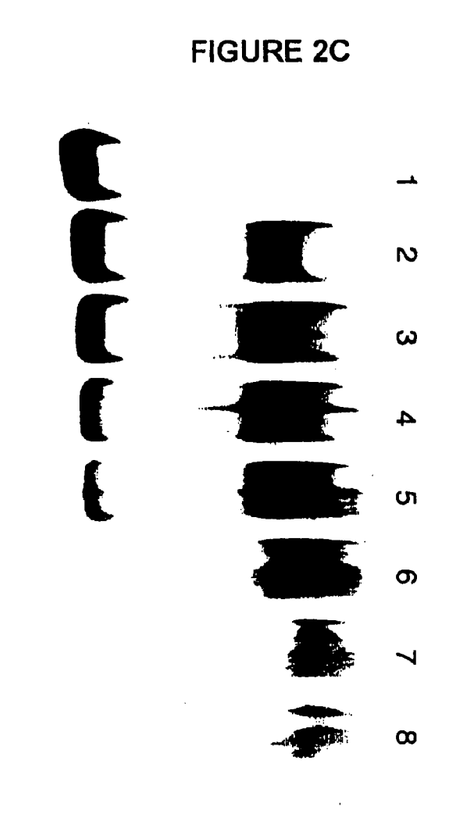

FIG. 2 shows gel shift binding studies on (A) CCTCC(b2)+d($A_3GGAGGA_3$), (SEQ ID NO.: 3) (B) CTCCT(b2)+d($A_3GAGGAA_3$) (SEQ ID NO.: 5) (lanes 1–4) and CTCCT(b2)+d($A_3AGGAGA_3$) (SEQ ID NO.: 4) (lanes 5–8), and (C) $T_5(b2)$-dimer+d($C_3T(TC_2)_2A_{10}C(TC_2)_3$) (SEQ ID NO.: 6). Solutions were made up by combining DNA (40 μM) with varying amounts of αPNA in 7.5 μL of TE-buffer. Before electrophoresis, 2.5 μL of loading buffer (0.01% xylene cyanol FF, 0.01% bromophenol blue solution, 60% (w/v) glycerol in running buffer) was added to the sample, mixed, and 3.5 μL of the sample was loaded onto the gel. Free DNA and αPNA-bound DNA were resolved by nondenaturing 14% PAGE in 44 mM Tris-borate, pH 7.2 for 1 hour at 14 V cm−1 at 4° C. The ratios of αPNA to DNA in (A) for lanes 1–8 are 0/1, 1/2, 3/4, 1/1, 5/4, 3/2, 7/4 and 2/1. Lane 9 represents only αPNA. The ratios in (B) for lanes 1–4 as well as 5–8 are 0/1, 1/1, 2/3, and 4/7. The ratios in (C) from lanes 1–8 are 0/1, 1/2, 1/1, 3/2, 2/1, 5/2, 3/1, and 4/1. Gels were developed using the PlusOne™ DNA silver staining kit (Pharmacia Biotech).

To investigate the stability of the αPNA•DNA hybrids as well as their binding stoichiometry and structure, both gel-shift mobility and circular dichroism (CD) titration studies were performed. For the complex between CCTCC(b2) and d($A_3GGAGGA_3$) (SEQ ID NO.: 3), a single new slower-migrating species corresponding to CCTCC(b2)•d($A_3GGAGGA_3$) was detected in the gel shift assay as shown in FIG. 2A. The intensity of the d($A_3GGAGGA_3$) (SEQ ID NO.: 3) band steadily decreased with increasing amounts of CCTCC(b2) until there was no unbound single-stranded DNA at an αPNA/DNA ratio of 1.5. The detection of a triplex between two CCTCC(b2)'s (net charge +6 each) and d($A_3GGAGGA_3$) (SEQ. ID NO.: 3) (net charge −10) is precluded on the grounds that the resultant terniary complex would have a net positive charge and therefore be expected to migrate towards the negative electrode. Evidence for duplex formation was also obtained from experiments on CTCCT(b2)+d($A_3GAGGAA_3$) ((SEQ. ID NO.: 5) and CTCCT(b2)+d($A_3AGGAGA_3$) (SEQ. ID NO.: 4) as shown in FIG. 2B. These gels also confirmed that the parallel (N/3') orientation resulted in stronger binding. No binding was observed between an "abasic" αPNA(b2) peptide Ac-Cys$_{Acm}$-Lys-(Ser-Ala$_2$-Lys)$_4$-Ser-Gly-Lys-NH$_2$ and d($TA_3G_5A_3T$) (SEQ. ID NO.: 1), which underscores the role that nucleobases play in αPNA molecular recognition. The concentration of this "abasic" αPNA(b2) was determined by quantitative ninhydrin analysis (Sarin, V. K.; Kent, S. B. H.; Tam, J. P.; Merrifield, R. B. *Anal. Biochem.*, 1981, 117, 147–157). Interestingly, the PAGE experiment with $T_5(b2)$-dimer (net charge +12) and d($C_3T(TC_2)_2A_{10}C(TC_2)_3$) (SEQ. ID NO.: 6) (net charge −29) produced an additional slower-moving species at the expense of the initially-formed species at αPNA/DNA ratios greater than 1 as shown in FIG. 2C. This result is consistent with the formation of a terniary complex.

Figure 3:
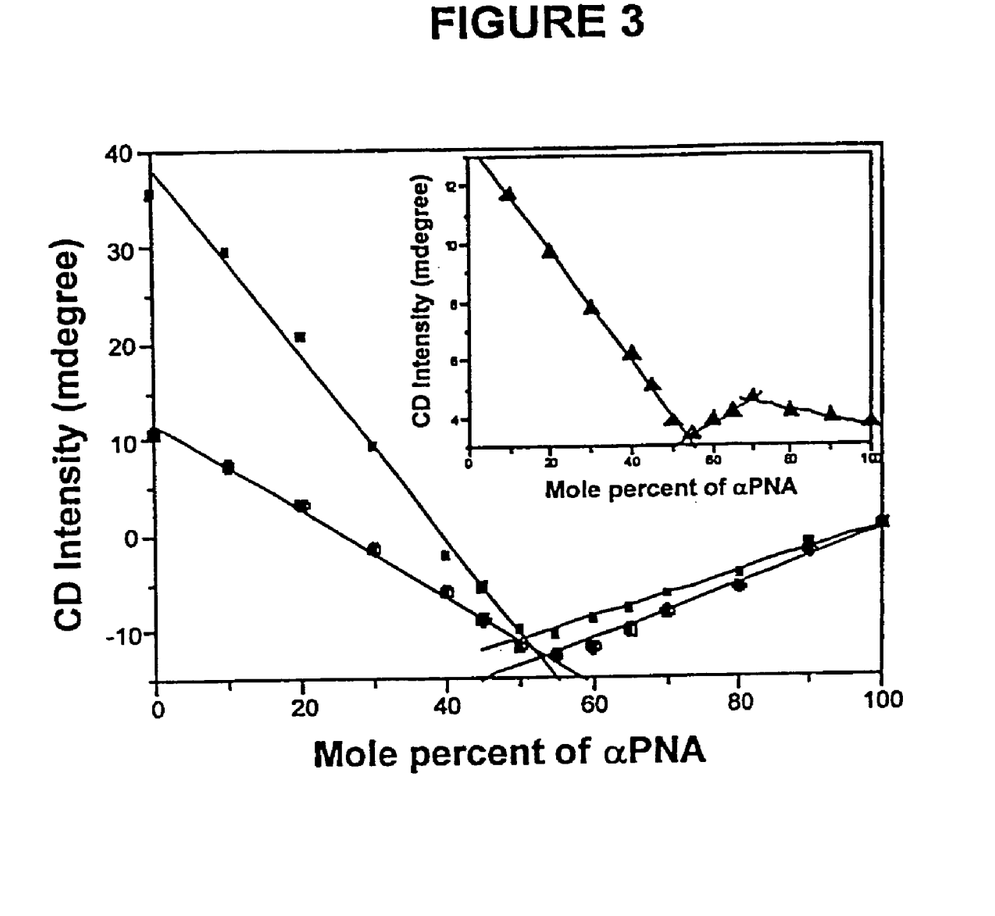
FIG. 3 is a chart showing circular dichroism (CD) intensity versus mole percent of the preferred αPNA.

FIG. 3 shows job plots for CDs of $C_5(b2)+d(TA_3G_5A_3T)$ (SEQ. ID NO.: 1) (at 258 nm, squares), CCTCC(b2)+d($A_3GGAGGA_3$) (SEQ. ID NO.: 3) (at 258 nm, circles), and $T_5(b2)$-dimer+d($A_{10}$) (SEQ. ID NO.: 2) (at 261 nm, triangles). Spectra were recorded at 5° C. using a JASCO J-600 CD spectro-polarimeter. Samples having a total concentration ([αPNA]+[DNA]) of 12 μM were made up in doubly deionized water and placed in a stoppered optical quartz cell (1 cm pathlength). Dry air was purged through the sample compartment. Each data point represents the average of eight (baseline corrected) points. FIG. 3 shows further support for the binding stoichiometries of the αPNA•DNA complexes comes from CD titration studies on $C_5(b2)+d(TA_3G_5A_3T)$ (SEQ. ID NO.: 1) and CCTCC(b2)+d($A_3GGAGGA_3$) (SEQ. ID NO.: 3), which both showed intensity minima at 50 mol % αPNA as expected for a 1:1 binding stoichiometry. The inset of FIG. 3 shows that in addition to a duplex, $T_5(b2)$-dimer+d($A_{10}$) (SEQ. ID NO.: 2) also showed evidence of a 2:1 complex. This is in line with the PAGE experiment with $T_5(b2)$-dimer and d($C_3T(TC_2)_2A_{10}C(TC_2)_3$) (SEQ. ID NO.: 6).

Figure 4:
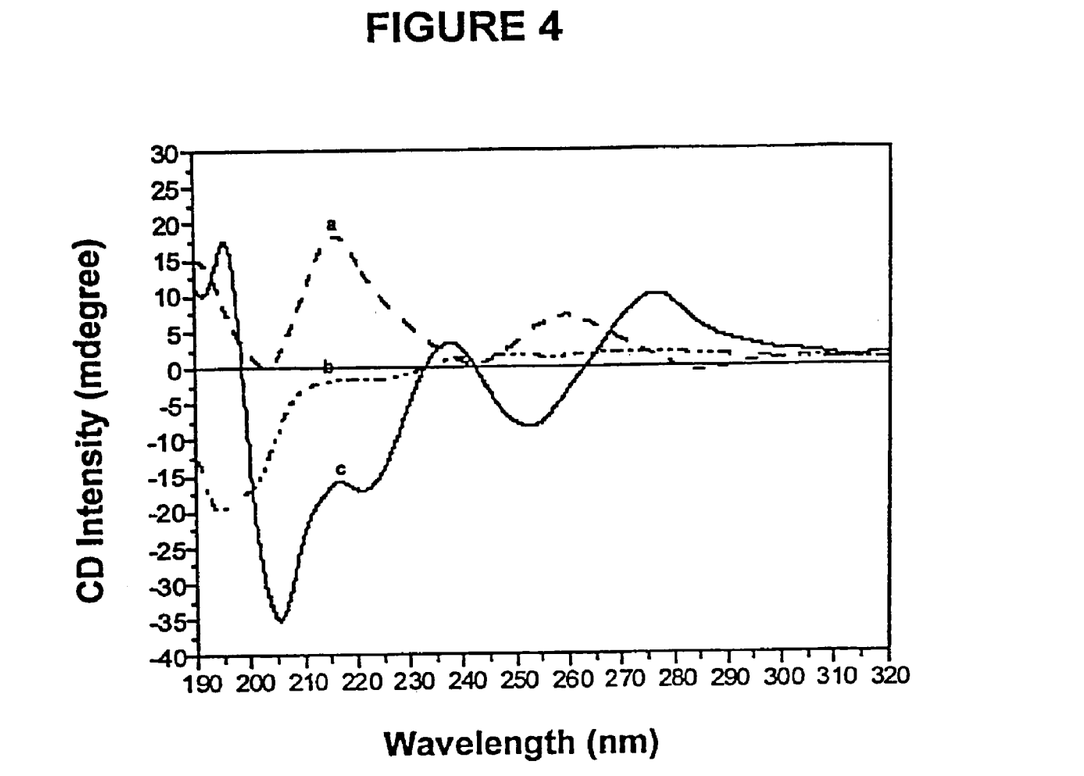
FIG. 4 is a chart showing CD intensity versus wavelength.

FIG. 4 shows the comparative CD spectra of (a) DNA d($A_3GGAGGA_3$) (SEQ. ID NO.: 3) alone, (b) αPNA CCTCC(b2) alone, and (c) a 1:1 mixture of d($A_3GGAGGA_3$) (SEQ. ID NO.: 3)+CCTCC(b2) (6 μM each) in distilled H$_2$O. Spectra were recorded as described in FIG. 3. In FIG. 4, the CD spectrum of a solution containing equimolar amounts of CCTCC(b2) and d($A_3GGAGGA_3$) (SEQ. ID NO.: 3) shows the characteristic CD signatures of both a peptide α-helix (minima at 220 and 206 nm, maximum at 196 nm) (Woody, R. M. *Methods Enzymol.* 1995, 246, 34–71) and a DNA B-helix (maximum at 280 and minimum at 255 nm). (Gray, D. M.; Ratliff, R. L.; Vaughan, M. R. *Methods Enzymol* 1992, 211, 389–406). Since control CD spectra show that the individual b2 αPNA and DNA components are essentially disordered in the absence of the other, it appears that they are each acting as templates for hybridization. Analogous behavior has been noted previously for peptides corresponding to the basic regions of DNA-binding proteins. (Patel, L.; Abate, C.; Curran, T. *Nature* 1990, 347, 572–575; Weiss, M. A.; Ellenberger, T.; Wobbe, C. R.; Lee, J. P.; Harrison, S. C.; Struhl, K. Ibid., 1990, 347, 575–578; Talanian, R. V.; McKnight, C. J.; Kim, P. S. *Science* 1990, 249,769–771).

Binding Affinity and Orientational Specificity Modulated by Hydrophobic N-Caps

The binding properties of a series of N-capped αPNAs that incorporated additional α-stacking interactions were examined. This experiment was based on the assumption that tighter binding would result if "end-fraying" of αPNAs were minimized by incorporating such interactions at one or both ends of the αPNA chain. Such an effect could be important since the described αPNA modules rely on only 5 base-pair interactions and end-fraying could adversely affect up to 50% (in CTTTC) of the interstrand Watson-Crick hydrogen-bonds. The enhancement of duplex stability through such α—α interactions had been demonstrated with unpaired "dangling" nucleobases at the 5'-ends of RNA, (M. Petersheim, D. H. Turner, *Biochemistry*, 1983, 22, 256–263) and analogous effects resulted when nucleobases as well as their unnatural aromatic counterparts were incorporated at the 5'-ends of DNA. (M. Senior, R. A. Jones, K. J. Breslauer *Biochemistry*, 1988, 27, 3879–3885; K. M. Guckian, B. A. Schweitzer, R. X.-F. Ren, C. J. Sheils, D. C. Tahmassebi, E. T. Kool, *J. Am. Chem. Soc.*, 2000, 122, 2213–2222).

It was found that N-capped αPNAs lead to both enhanced affinity as well as orientational specificity with complementary ssDNA targets. Unexpectedly, the observed N-cap effects in the preferred parallel series were found to be better correlated to hydrophobicity rather than π-stacking.

N-capped αPNAs were synthesized via the SPPS protocol but substituting an appropriate carboxylic acid in the N-capping step. All of the αPNAs possess the backbone shown in FIG. 1B and are described by the N-cap followed by the nucleobase sequence (N- to C-terminus from left to right). Electrospray ionization mass spectral (ESI$^+$-MS) characterization data for N-capped αPNAs: 4-phenylbutyryl-CTCCT calcd 2811.41, found 2812.61±0.41; 4-(p-methoxyphenyl) butyryl-CTCCT calcd 2841.42, found 2842.36±0.13; 4-(p-nitrophenyl)butyryl-CTCCT calcd 2856.40, found 2857.55±0.24; 4-(2-naphthyl)butyryl-CTCCT calcd 2861.43, found 2862.68±0.40; 4-(1-pyrenyl)butyryl-CTCCT calcd 2935.44, found 2937.02±0.39; n-butyryl-CTCCT calcd 2735.38, found 2736.52±0.54; n-hexanoyl-CTCCT calcd 2763.41, found 2766.01±1.19; 3-cyclopentylpropionyl-CTCCT calcd 2789.43 found 2792.10±1.01; 4-cyclohexylbutyryl-CTCCT calcd 2817.46, found 2818.41±0.74; 4-cyclohexylbutyryl-CCTCC calcd 2802.46, found 2803.12±0.39; 4-cyclohexylbutyryl-CCCCC calcd 2787.46, found 2787.83±0.06.

The N-caps investigated consisted of a series of arenyl and aliphatic carboxylic acids. Both sets of N-caps included a flexible methylene linker to allow for the anticipated cap-base interaction without significantly disrupting the complex structure. Thermal UV denaturation ($T_m$) data for the equilibria between N-cap-CTCCT and d($A_3$GAGGA$A_3$) (SEQ. ID NO.: 5) (N/5' or parallel orientation) and N-cap-CTCCT and d($A_3$AGGAG$A_3$) (SEQ. ID NO.: 4) (N/3' or antiparallel orientation) are collected in Table 2. Thermal UV denaturation curves were obtained with sample solutions made by combining the N-capped (αPNA and ssDNA components (5 μM each) in TE buffer (10 mM Tris-HCl, 1 mM EDTA, pH 7). These solutions were then incubated overnight at 4° C.

TABLE 2

| entry | cap-CTCCT | d($A_3$-GAGGA-$A_3$)[1] $T_m$ (heating, cooling) | d($A_3$-AGGAG-$A_3$)[2] $T_m$ (heating)[a] |
|---|---|---|---|
| 1. | cap = CH$_3$CO | 37.0, 32.0 | 32.0 |
| 2. | CH$_3$CH$_2$CH$_2$CO | 40.0, 36.7 | 30.2 |
| 3. | CH$_3$CH$_2$CH$_2$CH$_2$CH$_2$CO | 41.0, 35.0 | 33.4 |
| 4. | C$_5$H$_9$CH$_2$CH$_2$CO | 43.7, 38.2 | 33.8 |
| 5. | C$_6$H$_{11}$CH$_2$CH$_2$CH$_2$CO | 47.9, 43.7 | 33.4 |
| 6. | C$_6$H$_5$(CH$_2$)$_3$CO | 41.8, 38.5 | 33.6 |
| 7. | p-MeOC$_6$H$_4$(CH$_2$)$_3$CO | 41.3, 37.0 | 34.2 |
| 8. | p-NO$_2$C$_6$H$_4$(CH$_2$)$_3$CO | 41.6, 37.8 | 34.4 |
| 9. | 2-naphthyl(CH$_2$)$_3$CO | 42.7, 40.0 | 36.3 |
| 10. | 1-pyrenyl(CH$_2$)$_3$CO | 42.6, 43.8 | 39.0 |

[a]No cooperative transition was observed during the cooling cycle.
[1]SEQ ID NO.: 5
[2]SEQ ID NO.: 4

A number of interesting trends emerge from Table 2. First, all of the N-cap modifications resulted in higher $T_m$ values for the parallel αPNA•DNA complexes relative to the "parent" N-acetylated system. Reduced hysteresis was observed for all parallel complexes during the cooling cycle which was indicative of faster annealing kinetics. However, contrary to our expectations, the most striking enhancement occurred in the aliphatic N-cap series, with the 4-(cyclohexyl)butyryl-N-cap resulting in the highest $T_m$(heating, cooling) values (47.9, 43.7° C.). This represented an 11–12° C. increase compared to the parent N-acetylated αPNA. Such behavior would not be expected if π-stacking was the primary means of stabilizing these αPNA•DNA complexes. The relative insensitivity of 4-(phenyl)butyryl N-cap melting temperatures to electron-donating and electron-withdrawing phenyl substituents is consistent with this interpretation. (Cf. F. Cozzi, M. Cinquini, R. Annuziata, J. S. Siegel, *J. Am. Chem. Soc.* 1993, 115, 5330–5331).

Table 3 shows analogous $T_m$ enhancements with the symmetrical sequences N-4-(cyclohexyl)butyryl-CCTCC•d ($A_3$GGAGGA$_3$) (60.8, 51° C., entry 1) and N-4-(cyclohexyl)butyryl-CCCCC•d(TA$_3$GGGGG$A_3$T) (64.9, 66° C., entry 2), thus excluding the possibility that these trends were related solely to the base sequence. The incorporation of a single base-pair mismatch (N-4-(cyclohexyl)butyryl-CCTCC•d(TA$_3$GGGGG$A_3$T)) lowered the $T_m$ (heating, cooling) of the complex by 15 and 10° C. respectively (entry 3), which is consistent with our previous observations in the N-acetyl series and indicates that the N-cap effect is decoupled from base-pairing. This reduction in melting temperature presumably arises from residual hydration of the mismatched nucleobases and provides additional support for our proposed Watson-Crick binding model.

TABLE 3

| entry | αPNA•DNA complex | $T_m$ (heating, cooling) |
|---|---|---|
| 1. | C$_6$H$_{11}$(CH$_2$)$_3$CO-CCT CC<br>5' d($A_3$-GGAGG-$A_3$) 3' | 60, 51 |
| 2. | C$_6$H$_{11}$(CH$_2$)$_3$CO-CCC CC<br>5' d(TA$_3$-GGGGG-$A_3$T) 3' | 65, 66 |
| 3. | C$_6$H$_{11}$(CH$_2$)$_3$CO-CC T CC<br>5' d(TA$_3$-GG G GG-$A_3$T) 3' | 50, 46 |

Figure 5A:
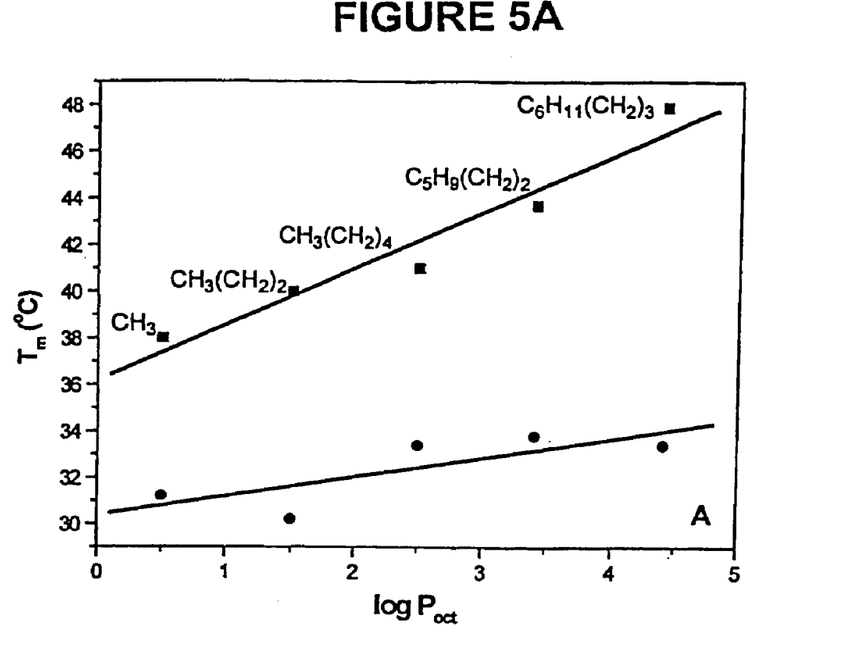
Figure 5B:
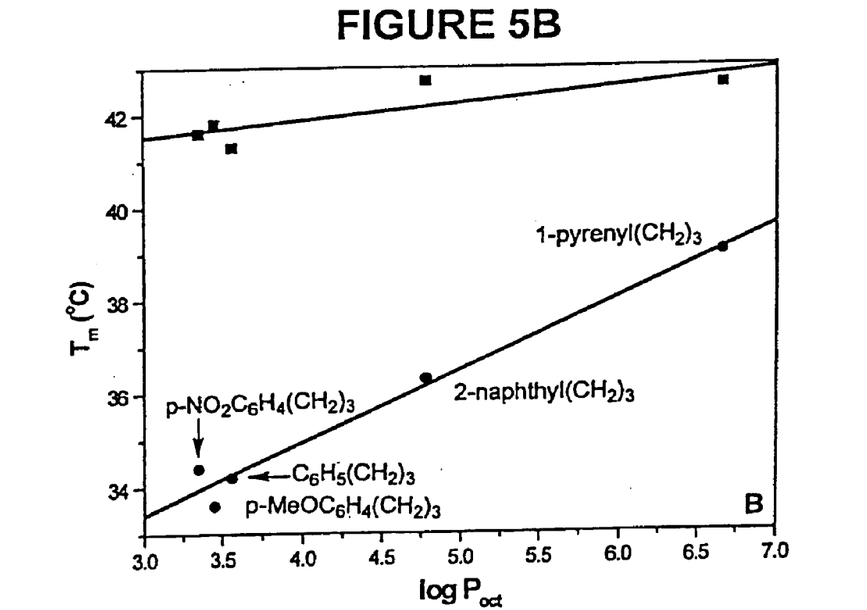

FIG. 5 shows a plot of $T_m$-versus calculated octanol-H$_2$O partition coefficients (log P values) for each N-cap. FIG. 5 shows that the melting temperatures of αPNA•DNA complexes is proportional to N-cap hydrophobicity. (A. Leo, C. Hansch, D. Elkins, *Chem. Rev.* 1971, 71, 525–616). It is likely that the strong dependence of $T_m$ on log P in the parallel aliphatic N-cap series is due to a combination of "classical" (entropically-driven) desolvation and "nonclassical" (enthalpically-driven) packing hydrophobic effects. (For a succinct introduction to the hydrophobic effect and its biological implications, see: A. Fersht, *Structure and Mechanism in Protein Science*; W. H. Freeman, New York, 1999, Chapter 11). For the antiparallel complexes, which exhibit uniformly lower $T_m$ values than their parallel counterparts, a weaker dependence is found for the arenyl N-caps. This suggests the existence of compensating π-stacking effects superimposed on the hydrophobic effects and is probably related to different overall structures (see CD data), but this is still conjecture that will have to await the completion of further αPNA•DNA structural studies. On the other hand, melting temperature is essentially independent of N-cap hydrophobicity in both the parallel-aromatic and antiparallel-aliphatic series. By demonstrating that strategically placed aliphatic groups can be used to modulate the affinity and orientational specificity of αPNA complexation to DNA, the repertoire of binding interactions available to these novel nucleic acid surrogates has been expanded. Others have noted similar stabilizing effects on oligonucleotide duplexes that were 5'-capped with aliphatic steroids. ((a) R. L. Letsinger, G. Zhang, D. K. Sun, T. Ikeuchi, P. S. Sarin, *Proc. Natl. Acad. Sci. USA* 1989, 86, 6553–6556. (b) S. M. Gryaznov, D. H. Loyd, *Nucleic Acid Res.* 1993, 21, 5909–5915. (c) C. F. Bleczinski, C. Richert, *J. Am. Chem. Soc.* 1999, 121, 10889–10894). However, our work provides a direct comparison between aliphatic and aromatic end-caps showing that—at least for αPNAs—aliphatic end-caps can have a stronger effect on hybridization than aromatic end-caps.

Figure 6A:
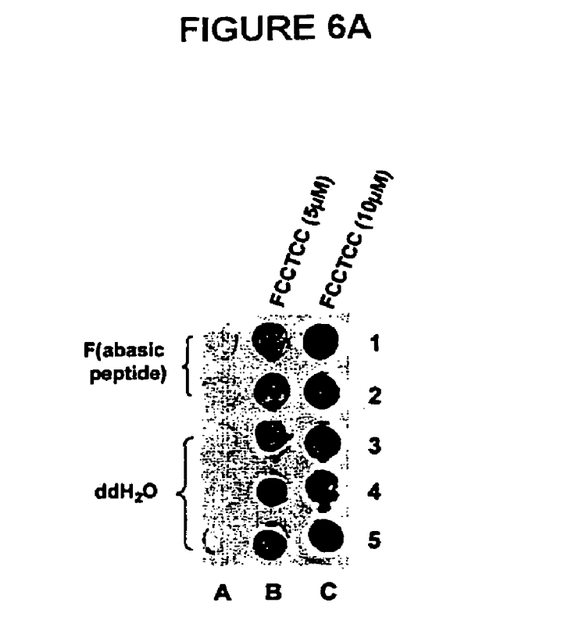
FIG. 6A shows a fluorescent image of a microtiter plate.
Figure 6B:
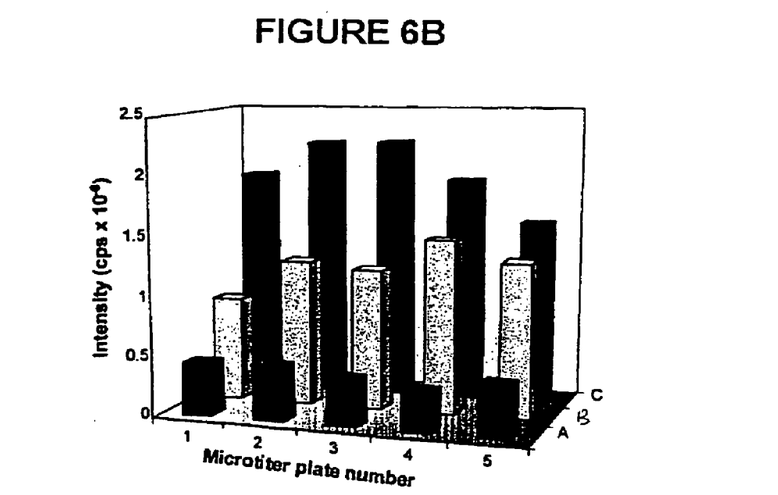
FIG. 6B shows shows the quantification of hybridization as a function of fluorescence intensity.

Assay for Determining Hybridization of αPNA and Single-Stranded Nucleic Acid Targets FIG. 6 shows a preferred hybridization of fluorescence-labeled αPNAs with gel-immobilized DNA d($A_4$GGAGG$A_4$) (SEQ. ID NO.: 7) on microtiter plate. A1–A2, 5 μM BODIPY® FLIA labeled abasic peptide; A3–A5, deionized water; B1–B5, 5 μM F—CCTCC; C1–C5, 10 μM F—CCTCC. a) Fluorescent image of the plate (FluorImager SI, Molecular Dynamics). b) Quantification of hybridization as a function of fluorescence intensity as determined with a FluorMax Plate Reader. Excitation wavelength: 480 nm; Emission wavelength: 512 nm. The ratio of the average intensity of C1–C5 to B1–B5 is 2 to 1 after subtracting the background A1–A5 signal.

Since the synthesized αPNAs incorporate a terminal Acm-protected cysteine residue, the thiol-reactive dye, BODIPY® FLIA, is introduced to Ac-Cys$_{Acm}$-Lys-(Ser$^C$-Ala$_2$-Lys)$_2$-Ser$^T$-(Ala$_2$-Lys-Ser$^C$)$_2$-Gly-Lys-NH$_2$ (CCTCC) after SPPS. The course of the labeling reaction can be easily followed by analytical HPLC and only a single HPLC purification is needed for the whole process. Based on comparative UV, CD, and PAGE experiments conducted with both labeled and unlabeled CCTCC and d($A_3$GGAGG$A_3$) (SEQ. ID NO.: 3), it was concluded that BODIPY has little effect on the complex stability or conformation and is thus suitable for in situ hybridization assays. Commercially obtained oligonucleotide d($A_3$GGAGG$A_3$) (SEQ. ID NO.: 3) containing a 5'-terminal acrylamide groups was immobilized on a 96 well microtiter plate following the procedure developed by Mosaic Technologies. (Rehman, F. N.; Audeh, M.; Abrams, E. S.; Hammond, P. W.; Kenney, M.; Boles, T. C. *Nucleic Acids Res.*, 1999, 27, 649–655).

After immobilization, a standard silver stain was applied and the dark color obtained proved that the acryldite DNA was immobilized on the gel. The spots may also be quantified by a gel documentation system. As a control, BODIPY labeled abasic peptide with unmodified Ser residues was synthesized as well. The results shown in FIG. 1 shows that αPNA binding to the immobilized DNA is not a consequense of the fluorescence tag. The signal that the FluroMax Reader and FluorImager SI detected was all due to the Watson-Crick base-pairing. Only the F-CCTCC shows the particular fluorescence emission spectra of the BODIPY dye (data not shown). If we consider the readings for F-labeled abasic peptide and water as background, the ratio of the average fluorescence intensity only depends on the concentration of the αPNA. Since the concentration of immobilized DNA is larger than that of added αPNA, this correlation shows that the hybridization assay is quantitative for bound αPNA.

The invention has been described with reference to the preferred embodiment. Obviously, modifications and alterations will occur to others upon reading and understanding of the preceding detailed description. It is intended that the invention be construed as including all such alterations and modifications insofar as they come within the scope of the appended claims or equivalents thereof.

The invention claimed is:

1. A peptide-based nucleic acid surrogate comprising:
a secondary structure; and
a $(AA^B\text{-}aa_n)_m$ subunit, wherein AA is a hydroxyl-amino acid, B is a nucleobase, aa is an amino acid, $n \geq 1$, and $m \geq 1$.

2. The peptide-based nucleic acid surrogate of claim 1, wherein the secondary structure is an alpha-helical structure.

3. The peptide-based nucleic acid surrogate of claim 1, wherein B is thymine, cytosine, adenine, guanine, and uracil.

4. The peptide-based nucleic acid surrogate of claim 1, wherein $m \geq 5$.

5. The peptide-based nucleic acid surrogate of claim 1, wherein the surrogate further comprises a protecting group.

6. The peptide-based nucleic acid surrogate of claim 5, wherein the protecting group is a base-labile fluorenyl methoxycarbonyl protecting group for an N-terminus amine of the peptide-based nucleic acid surrogate.

7. The peptide-based nucleic acid surrogate of claim 5, wherein the protecting group is an $I_2$-labile acetamidomethyl protecting group for the cysteine side chain amino acid.

8. The peptide-based nucleic acid surrogate of claim 1, wherein B is a purine nucleobase selected from the group consisting of adenine, 6-chloro-2-aminopurine and guanine.

9. The peptide-based nucleic acid surrogate of claim 8, wherein the purine nucleobase further comprises an acid-labile tert-butoxycarbonyl protecting group.

10. The peptide-based nucleic acid surrogate of claim 1, wherein the surrogate selectively binds with a nucleic acid target.

11. The peptide-based nucleic acid surrogate of claim 1, wherein an N-terminus of the surrogate comprises a carboxylic acid.

12. A peptide-based nucleic acid surrogate comprising:
an alpha-helical secondary structure;
a protecting group; and
a $(AA^B\text{-}aa_n)_m$ subunit, wherein AA is a hydroxyl-amino acid, B is a nucleobase, aa is an amino acid, $n \geq 1$, and $m \geq 1$.

13. The peptide-based nucleic acid surrogate of claim 12, wherein B is thymine, cytosine, adenine, guanine, and uracil.

14. The peptide-based nucleic acid surrogate of claim 12, wherein $m \geq 5$.

15. The peptide-based nucleic acid surrogate of claim 12, wherein the protecting group is a base-labile fluorenyl methoxycarbonyl protecting group for an N-terminus amine of the peptide-based nucleic acid surrogate.

16. The peptide-based nucleic acid surrogate of claim 12, wherein the protecting group is an $I_2$-labile acetamidomethyl protecting group for the cysteine side chain amino acid.

17. The peptide-based nucleic acid surrogate of claim 12, wherein B is a purine nucleobase selected from the group consisting of adenine, 6-chloro-2-aminopurine and guanine.

18. The peptide-based nucleic acid surrogate of claim 17, wherein the purine nucleobase further comprises an acid-labile tert-butoxycarbonyl protecting group.

19. The A method of forming a dimer from two peptide-based nucleic acid surrogates, each surrogate having a secondary structure, comprising the steps of:
solid-phase peptide synthesis of two resin-bound peptide-based nucleic acid surrogates, each surrogate having a secondary structure;
cleaving the resin from each peptide-based nucleic acid surrogate;
thiol deprotection of each peptide-based nucleic acid surrogate; and
disulfide bonding of the two peptide-based nucleic acid surrogates having a secondary structure to form a dimer.

20. The method of claim 19, wherein the secondary structure is an alpha-helical structure.

21. A method of forming a peptide-based nucleic acid surrogate having a secondary structure comprising the steps of:
solid-phase peptide synthesis of a resin-bound peptide-based nucleic acid surrogate;
cleaving the resin from the peptide-based nucleic acid surrogate; and
capping an N-terminus of the peptide-based nucleic acid surrogate with a carboxylic acid.

* * * * *

SEQUENCE LISTING

<160> NUMBER OF SEQ ID NOS: 7

<210> SEQ ID NO 1
<211> LENGTH: 13
<212> TYPE: DNA
<213> ORGANISM: Artificial
<220> FEATURE:
<223> OTHER INFORMATION: Synthesized

<400> SEQUENCE: 1 taaagggga aat

```
<210> SEQ ID NO 2
<211> LENGTH: 10
<212> TYPE: DNA
<213> ORGANISM: Artificial
<220> FEATURE:
<223> OTHER INFORMATION: Synthesized

<400> SEQUENCE: 2
aaaaaaaaaa                                                            10

<210> SEQ ID NO 3
<211> LENGTH: 11
<212> TYPE: DNA
<213> ORGANISM: Artificial
<220> FEATURE:
<223> OTHER INFORMATION: Synthesized

<400> SEQUENCE: 3
aaaggaggaa a                                                          11

<210> SEQ ID NO 4
<211> LENGTH: 11
<212> TYPE: DNA
<213> ORGANISM: Artificial
<220> FEATURE:
<223> OTHER INFORMATION: Synthesized

<400> SEQUENCE: 4
aaaaggagaa a                                                          11

<210> SEQ ID NO 5
<211> LENGTH: 11
<212> TYPE: DNA
<213> ORGANISM: Artificial
<220> FEATURE:
<223> OTHER INFORMATION: Synthesized

<400> SEQUENCE: 5
aaagaggaaa a                                                          11

<210> SEQ ID NO 6
<211> LENGTH: 30
<212> TYPE: DNA
<213> ORGANISM: Artificial
<220> FEATURE:
<223> OTHER INFORMATION: Synthesized

<400> SEQUENCE: 6
cccttcctcc aaaaaaaaaa ctcctcctcc                                      30

<210> SEQ ID NO 7
<211> LENGTH: 13
<212> TYPE: DNA
<213> ORGANISM: Artificial
<220> FEATURE:
<223> OTHER INFORMATION: Synthesized

<400> SEQUENCE: 7
aaaaggagga aaa                                                        13
```